(12) United States Patent
Francois et al.

(10) Patent No.: US 6,875,170 B2
(45) Date of Patent: Apr. 5, 2005

(54) POSITIONING, EXPLORATION, AND/OR INTERVENTION DEVICE, IN PARTICULAR IN THE FIELD OF ENDOSCOPY AND/OR MINI-INVASIVE SURGERY

(75) Inventors: Christian Francois, Paris (FR); Frank Boudghene, Fontenay-Sous-Bois (FR); Pierre Joli, Montigny-sur-Loing (FR)

(73) Assignee: Universite Pierre et Marie Curie, Paris (FR)

( * ) Notice: Subject to any disclaimer, the term of this patent is extended or adjusted under 35 U.S.C. 154(b) by 61 days.

(21) Appl. No.: 10/274,454

(22) Filed: Oct. 21, 2002

(65) Prior Publication Data

US 2003/0149338 A1 Aug. 7, 2003

Related U.S. Application Data

(63) Continuation-in-part of application No. PCT/FR01/01050, filed on Apr. 6, 2001.

(30) Foreign Application Priority Data

Apr. 21, 2000 (FR) .............................................. 00 05179

(51) Int. Cl.⁷ ................................................. A61B 1/00
(52) U.S. Cl. ....................... 600/141; 600/144; 600/152; 600/142; 604/95.03
(58) Field of Search ................................ 600/139–146, 600/152; 604/95.01, 95.03

(56) References Cited

U.S. PATENT DOCUMENTS

| 4,140,126 A | | 2/1979 | Choudhury ................. 128/325 |
| 4,676,228 A | * | 6/1987 | Krasner et al. ............. 600/116 |
| 4,794,912 A | | 1/1989 | Lia ............................... 128/4 |
| 4,832,473 A | * | 5/1989 | Ueda ........................... 359/367 |
| 4,893,613 A | * | 1/1990 | Hake ........................... 600/152 |
| 5,042,707 A | | 8/1991 | Taheri ........................ 606/213 |
| 5,179,934 A | | 1/1993 | Nagayoshi et al. ............ 128/4 |
| 5,203,319 A | | 4/1993 | Danna et al. .................. 128/4 |
| 5,531,686 A | | 7/1996 | Lundquist et al. ............ 604/95 |
| 5,591,195 A | | 1/1997 | Taheri et al. ............... 606/194 |
| 6,162,171 A | * | 12/2000 | Ng et al. ..................... 600/141 |

FOREIGN PATENT DOCUMENTS

| EP | 0 788 807 | 8/1997 |
| EP | 0 790 066 | 8/1997 |
| EP | 0 900 575 | 3/1999 |
| EP | 0 904 796 | 3/1999 |
| FR | 2 659 397 | 9/1991 |
| WO | 95/18311 | 7/1995 |
| WO | 96/35877 | 11/1996 |
| WO | 97/26936 | 7/1997 |
| WO | 98/31944 | 7/1998 |
| WO | 99/22798 | 5/1999 |

OTHER PUBLICATIONS

Dario et al.; A miniature steerable end–effector for application in an integrated system for computer–assisted arthroscopy; Proceedings of the 1997 IEEE; pp 1573–1579.

Dario et al.; A micro robotic system for colonoscopy; Proceedings of the 1997 IEEE; pp 1567–1572.

* cited by examiner

*Primary Examiner*—Beverly M. Flanagan
(74) *Attorney, Agent, or Firm*—Jacobson Holman PLLC

(57) ABSTRACT

The positioning, intervention, and/or exploration device has two endpieces (6a–6d, 7) and at least one cable (20) extending from one endpiece to the other (6a–6d, 7), it has at least two bellows (10) each fixed directly to both of the endpieces and it has means (12, 18) for modifying the pressure of a fluid in each of the bellows independently of the other bellows.

27 Claims, 6 Drawing Sheets

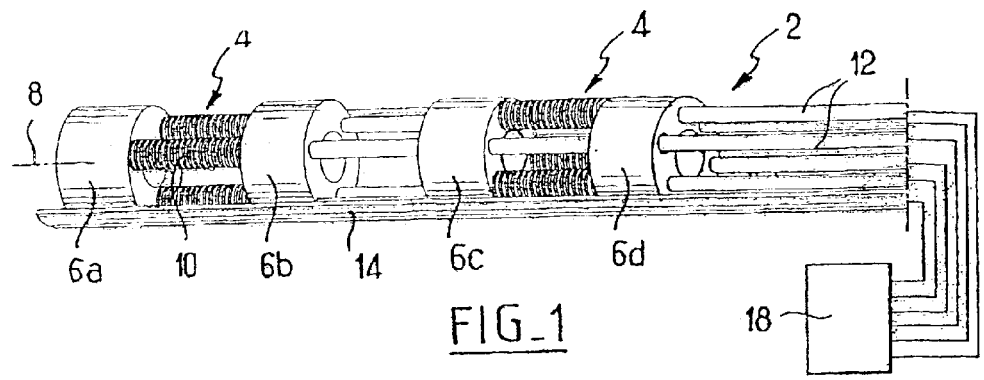
FIG_1
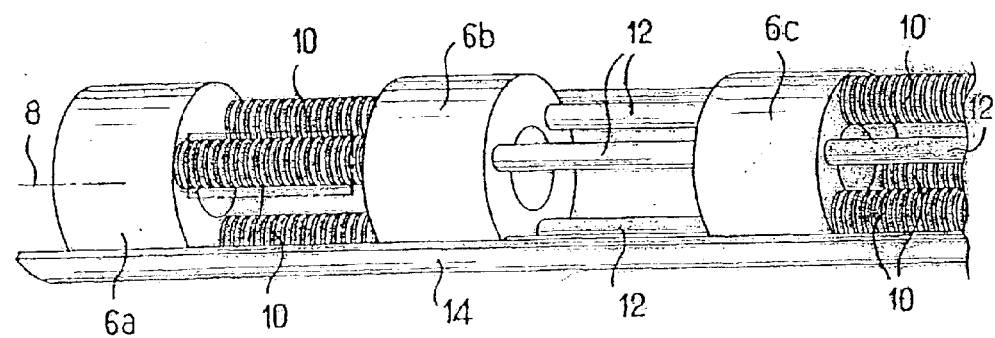
FIG_2
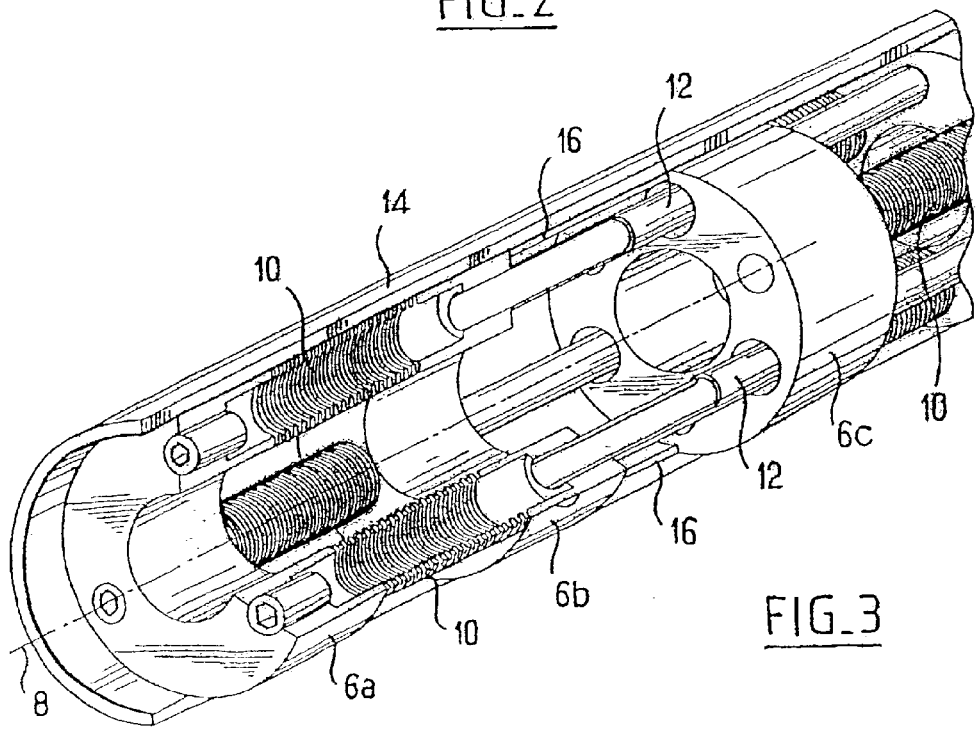
FIG_3

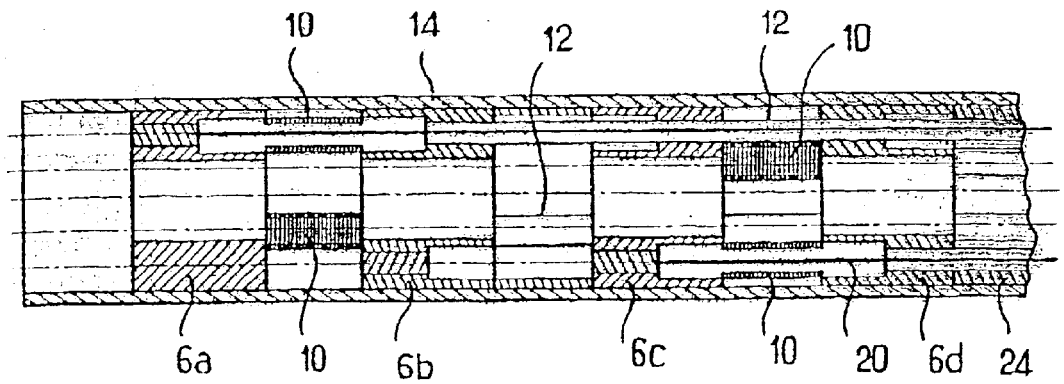
FIG_4
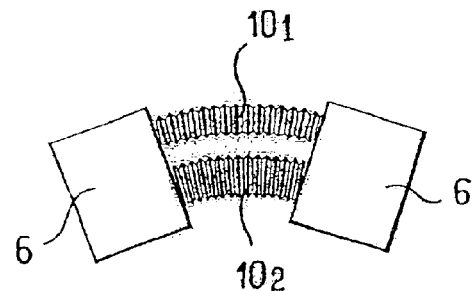
FIG_5
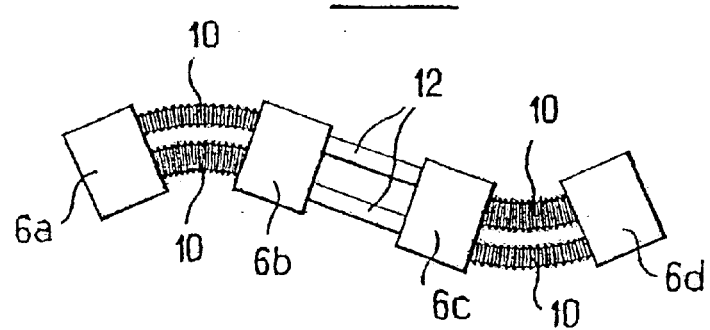
FIG_6

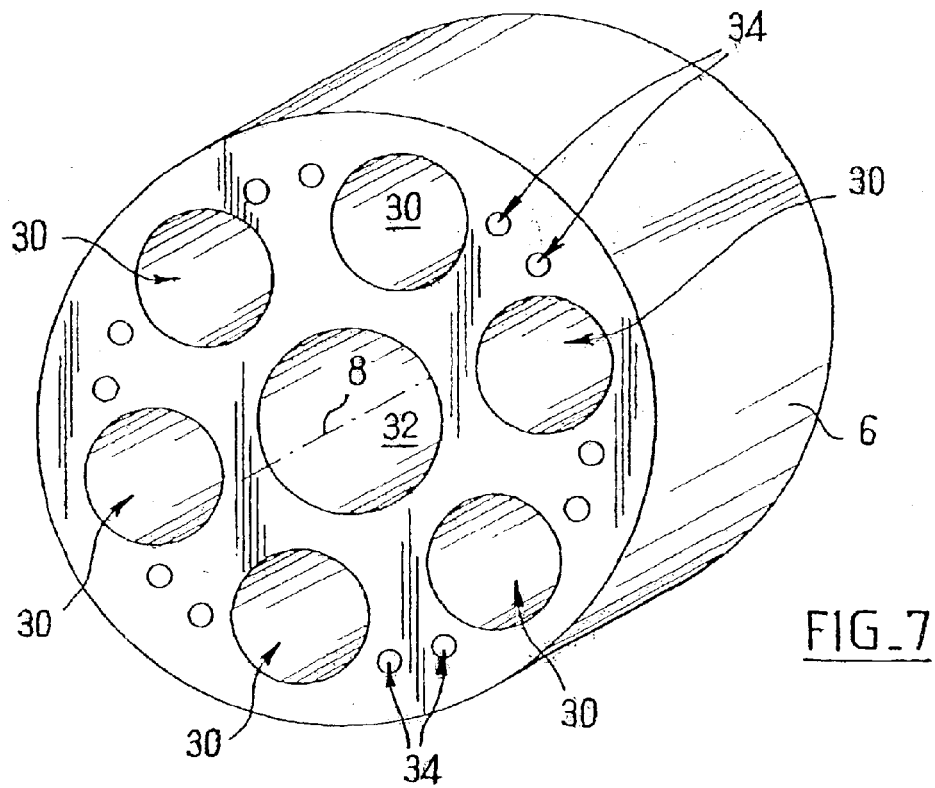
FIG_7
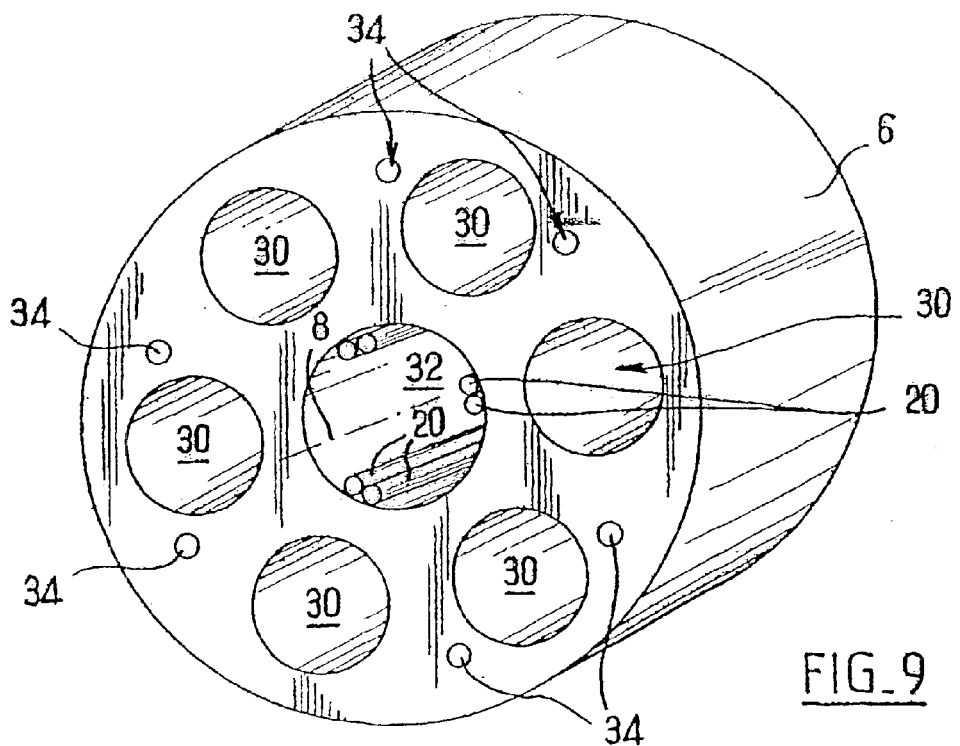
FIG_9

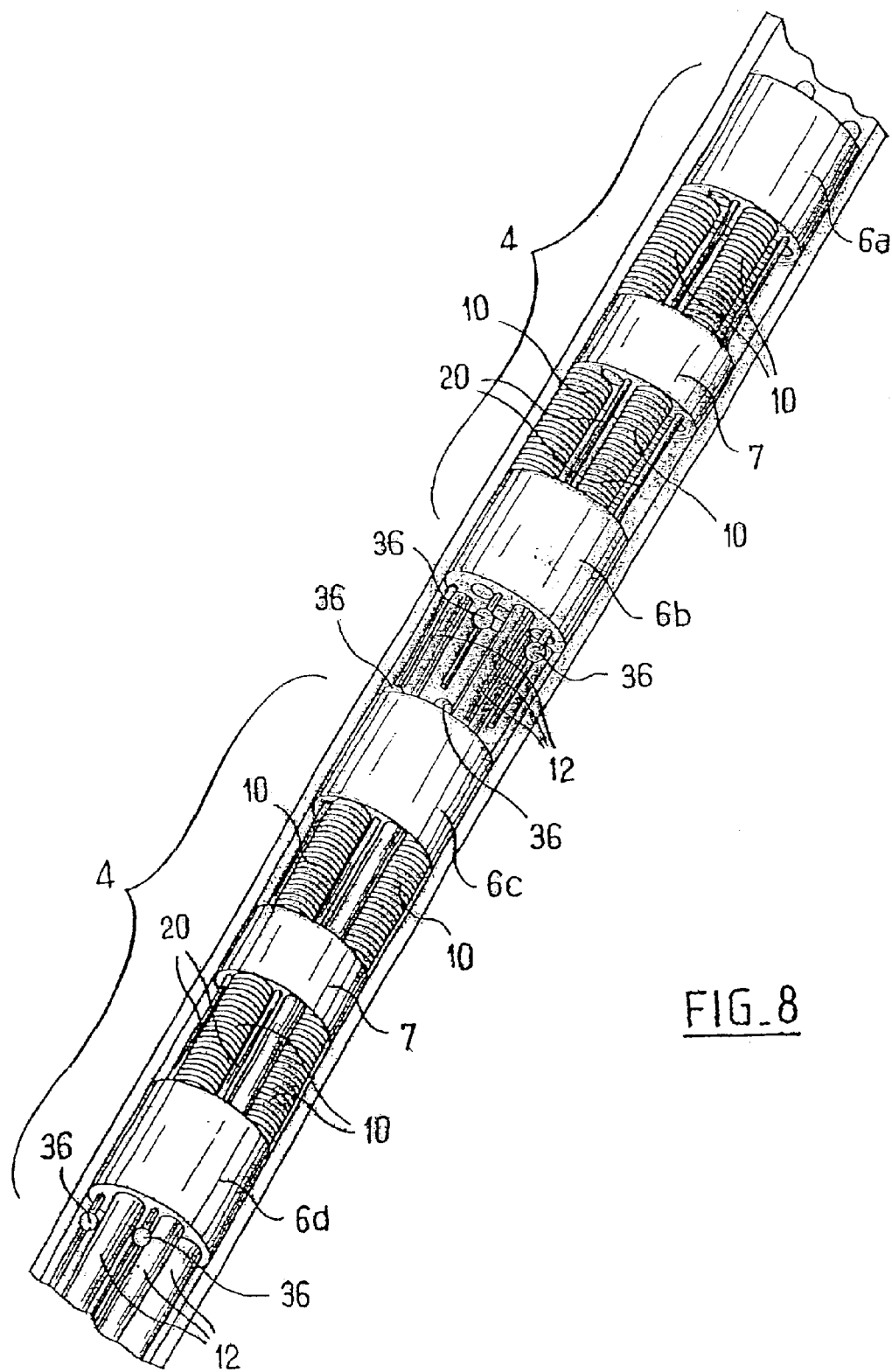
FIG_8

POSITIONING, EXPLORATION, AND/OR INTERVENTION DEVICE, IN PARTICULAR IN THE FIELD OF ENDOSCOPY AND/OR MINI-INVASIVE SURGERY

This is a Continuation-in-Part of PCT/FR01/01050 filed on Apr. 6, 2001 and published in French.

The invention relates to positioning, exploration, and/or intervention devices in particular for medico-surgical instruments such as catheters, endoscopes, or celiolaparoscopes. It also relates to various industries that may need to use devices of this type of a size that can lie in the range a few millimeters to several decimeters.

Medical and surgical instruments such as endoscopes or catheters are known for penetrating into ducts or cavities of the human body (vessels, digestive or urinary tract, etc.) for observation or intervention purposes. One of the main difficulties raised by such instruments is that they must be capable of deforming so as to follow the curvature of the duct or cavity along which they are progressing or so as to take one of two paths at a branch or so as to avoid an obstacle, and this must damage tissue as little as possible. The problem arises, for example, when it is desired to treat an aneurysm by installing an aortic prosthesis. For this purpose, instruments are known which are deformed by means of internal cables that are pulled or pushed so as to curve the instrument in one direction or the other. That applies for example to document EP-0 788 807. Nevertheless, instruments curved by pulling on cables cannot take up very sharp curves which can make progress complicated. Furthermore, those instruments often lack flexibility and are too rigid. The document "A micro-robotic system for colonoscopy", Proceedings of the 1997 IEEE Internal Conference on Robotics and Automation, Albuquerque, N.Mex., April 1997, presents an instrument whose body is made with a bellows enabling it to be lengthened or shortened at will, and capable of advancing like a worm in a duct. However, that device still does not make it possible to impart a predetermined sharp curvature to the instrument.

In another context, numerous industrial applications require the lack of accuracy of machines or robots to be made good by a device for fine repositioning of an end tool or of a part being carried. For example, it can be necessary to align marks on two parts to be engaged one in the other (repositioning during insertion), or else to minimize contact forces between a tool and a workpiece (e.g. removing flash).

Three types of system are used for this purpose:
traditional precision mechanical devices combining axes for translation and for rotation, with movement being driven on the basis of relative location information delivered by external position detectors. By way of example, mention can be made of readjusting a laser beam on its trajectory while welding two pieces together. Under such circumstances, information concerning positioning error between the join plane to be followed and the real position of the laser beam that results from the programmed nominal trajectory is supplied by a camera situated upstream from the beam;
passive compliant devices. These are elastic mechanical systems which deform under the action of external contact forces between the tool or the piece it is carrying and the piece to be machined or the receiver piece. The disposition of the deformable elastic elements and the stiffness thereof are chosen in such a manner that the movements of the end member (tool or piece carried thereby) minimize the contact forces in all directions along the programmed nominal trajectory; and active compliant devices. These are mechanical systems fitted with internal actuators which control the movements of the end member as a function of contact force values supplied by force sensors integrated in the system. In that case also, the idea is to minimize contact forces along the programmed trajectory.

In those fields also, it is desirable to have a positioning, exploration, and/or intervention device that is capable of combining a large amount of controlled curvature with flexibility.

An object of the invention is to provide a positioning, exploration, and/or intervention device that is suitable for being controlled to obtain pronounced curvature while nevertheless being capable of presenting substantial flexibility.

According to the invention, in order to achieve this object, there is provided a positioning, intervention, and/or exploration device having two endpieces and at least one cable extending from one endpiece to the other, the device comprising at least two bellows each fixed directly to the two endpieces, and means for modifying the pressure of a fluid in each of the bellows independently of the other bellows.

Thus, the two bellows make it possible to modify the length of the device by modifying the pressure in each of the bellows while conserving equal pressures between the bellows at all times. It is thus possible to lengthen or shorten the device. In addition, the pressures in the bellows can be made to be different from each other in order to curve the device. It is also possible to combine these two types of movement. It is found in practice that the bellows enable the device to obtain sharper curvature than is possible in conventional devices controlled solely by cable. This is due in particular to the fact that curvature can be the result both of high pressure in one bellows and low pressure in another bellows, whereas the cables of known devices work essentially in traction only. Furthermore, the device is deformed by acting on the existence and the amplitude of a pressure difference, i.e. by controlling relative pressure. However, the device also makes it possible to select the absolute pressures that exist in the bellows so as to vary the flexibility or the stiffness of the device. Thus, working with high pressures makes the device rigid against external forces. In contrast, working with low pressures makes the device relatively flexible, deformable, and of little danger to its surroundings, which is a significant advantage for applications in the medical field. Controlling pressure makes it possible to vary the stiffness of the device at will. In particular, the device can be given maximum stiffness or on the contrary maximum flexibility. That is why such a positioning, exploration, and/or intervention device is particularly advantageous in the medical field (surgery, . . . ) as well as in numerous industries.

Furthermore, the curvature of the device is thus controlled at will by the bellows and/or by one or more cables.

Advantageously, the device comprises at least three bellows each fixed to both endpieces.

Thus, the device can be curved in any direction.

Advantageously, the device includes at least one cable extending from one endpiece to the other.

Advantageously, the or each cable is fixed to at least one of the endpieces and/or is movable relative to at least one of the endpieces.

Advantageously, the or each cable is off-center relative to the longitudinal axis of the device.

Advantageously, the or each cable extends outside the bellows.

Advantageously, the device includes feed tubes for feeding the bellows with fluid, the or each cable passing outside the tubes.

Advantageously, the or each cable carries at least one block suitable for coming into abutment against at least one of the endpieces during certain deformations of the device.

Advantageously, the or each cable carries at least two blocks suitable for coming into abutment in two opposite directions against the two endpieces.

Advantageously, the cables are two in number per bellows and are disposed on either side of the bellows.

Advantageously, the device has at least three endpieces disposed in succession, and for each successive pair of endpieces, it has at least two bellows each fixed to two endpieces.

The device thus presents at least two stages whose curvatures can be added or combined.

Advantageously, for each successive pair or endpieces the device includes means for modifying the pressure of a fluid in each of the bellows fixed to the endpieces of the pair, and for doing so independently of the other bellows fixed to the endpieces of the pair.

Advantageously, the means for modifying the pressure are suitable for modifying the pressure in each of the bellows fixed to the endpieces of one of the pairs, and for doing so independently of the bellows fixed to the endpieces of the other pair or of another pair amongst the pairs of endpieces.

Advantageously, the two bellows of one of the pairs of endpieces are in fluid communication with the respective bellows of the other pair or of another pair amongst the pairs of endpieces.

Advantageously, the device includes at least one spacer disposed to prevent two endpieces moving closer together or to prevent two of the endpieces moving closer together beyond a predetermined value.

Advantageously, each bellows is capable of lengthening and of shortening along a longitudinal direction of the bellows under the effect of the fluid without substantial modification of the dimension of the bellows perpendicularly to the longitudinal direction.

Thus, the bends of two stages can be in different planes or they can be in the same plane. Under such circumstances, they can extend in the same direction or in opposite directions.

Advantageously, the device has an inner first sheath fixed to a proximal one of the endpieces, and an outer second sheath receiving the endpieces and suitable for sliding in the inner first sheath.

Thus, the length of the device can be modified by acting on the bellows without harming sealing between the outside and the inside of the device.

Advantageously, the fluid is a liquid.

Advantageously, variations in liquid pressure or in cable tension can be combined so as to modify the stiffness and the orientation of the device.

Advantageously, the device has an empty longitudinal space extending from one end of the device to the other.

This space can receive elements for intervention, observation, etc.

Advantageously, the empty longitudinal space allows instruments or waveguides to be passed therealong.

The invention also provides a medico-surgical instrument including a device of the invention for positioning, exploration, and/or intervention.

Advantageously, it is a catheter.

Advantageously, it is an endoscope.

Other characteristics and advantages of the invention appear further in the following description of two preferred embodiments and of variants given as non-limiting examples. In the accompanying drawings:

FIGS. 1 and 2 are two perspective views of a positioning device constituting a first embodiment of the invention;

FIG. 3 is a partially cutaway perspective view of the FIG. 1 device;

FIG. 4 is an axial section view of a positioning device constituting a second embodiment of the invention;

FIGS. 5 and 6 show deformation in curvature respectively of one and of two stages of the devices of the preceding figures;

FIG. 7 is a view of an endpiece of a device constituting a third embodiment of the invention;

FIG. 8 is a perspective view of the device of the third embodiment;

FIG. 9 is a view similar to FIG. 7 showing a fourth embodiment of the invention;

Figure 10:
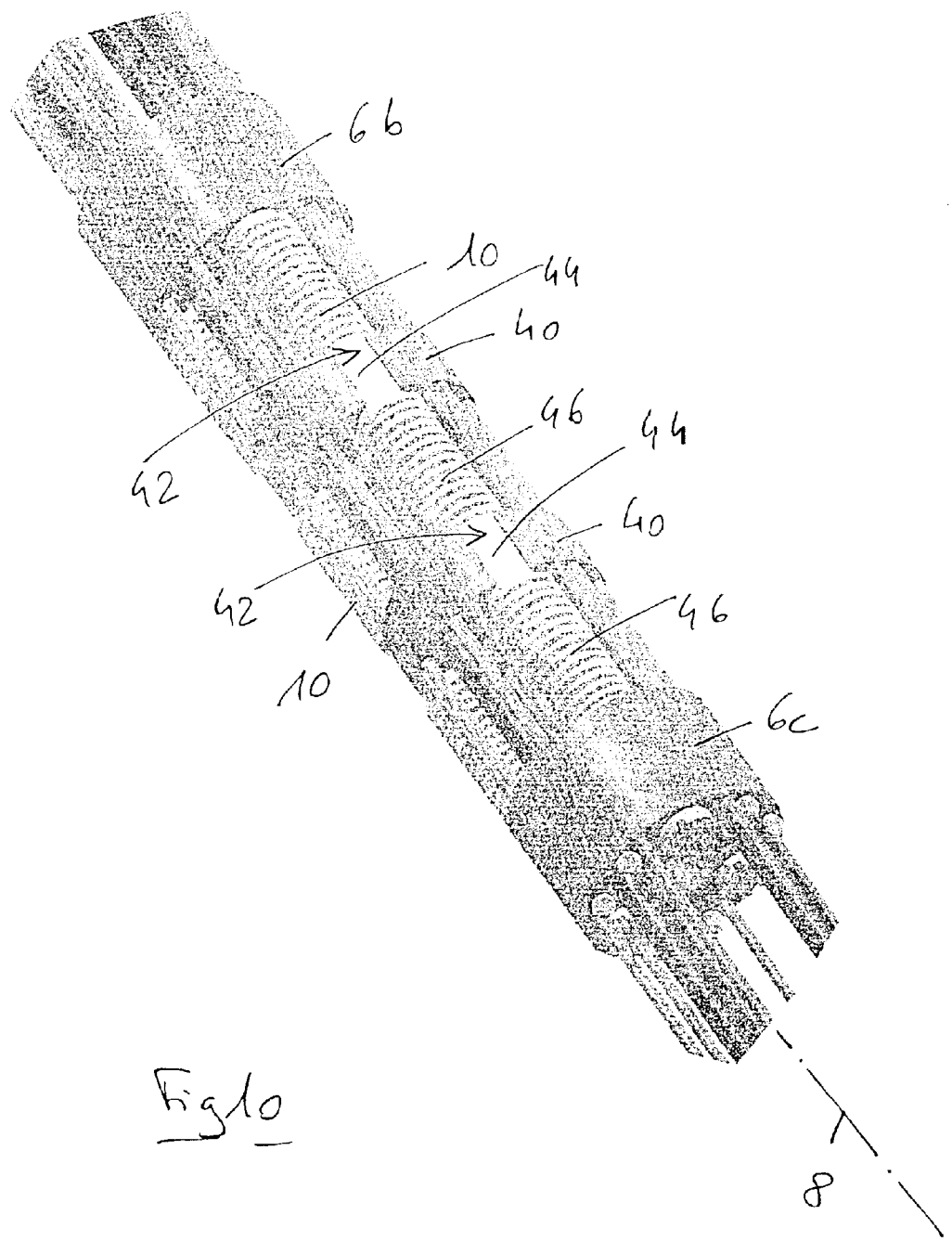
FIG. 10 is a view similar to FIG. 3 showing a fifth embodiment of the invention.

A first embodiment of the invention is described with reference to FIGS. 1 to 3. In this case, the positioning device 2 has two modules or stages 4. Each stage 4 has two endpieces 6 in the form of solid cylinders pierced by ducts as explained below. All four endpieces 6 are identical and they are placed in succession along a common axis 8. The successive endpieces are referenced 6a, 6b, 6c, and 6d. The endpiece 6a is the distal endpiece corresponding to the free end of the device. The endpiece 6d is the proximal endpiece and is the endpiece closest to the fluid control and feed means 18 of the device.

The endpieces 6a and 6b form one pair while the endpieces 6c and 6d form another pair. Each of these two pairs is associated with a plurality of bellows 10, there being three bellows for each pair in this case. All six bellows 10 are identical. They are generally in the form of elongate cylinders parallel to the axis 8. The three bellows for each pair of endpieces are uniformly distributed around the axis 8. Each bellows has its ends fixed to the two endpieces of the corresponding pair, and specifically to axial end faces thereof. The distal axial end of each bellows is closed.

The device has six ducts 12, one for each bellows 10, all of the ducts extending parallel to the axis 8. Three of the ducts terminate in the proximal endpiece 6d via its proximal axial end face remote from the bellows. They pass through the endpiece 6d and are in fluid communication inside the endpiece with the proximal axial ends of three respective bellows. The other three ducts 12 pass through the two endpieces 6d and 6c at regular spacing around the axis 8, each being positioned between two adjacent bellows of that pair of endpieces. These three ducts are free to slide through orifices in the two endpieces 6c and 6d. Thereafter, the three ducts pass through the space between the two modules 4 and reach the proximal end of the endpiece 6b.

The radial positioning and the spacing of these ducts can be chosen so as to leave a central channel of greater or smaller diameter and a peripheral space of greater or smaller size enabling a folded annular sleeve (endoprosthesis) to be received possibly together with a release device therefor (inflatable balloon). Inside the endpiece 6b, the ducts are put into fluid communication with the three bellows 10 associated with said endpiece. It follows from the above arrangement that the two groups of three bellows are offset from each other by one-sixth of a turn about the axis 8, in axial view. The six ducts 12 can be uniformly distributed around the axis 8. The same applies to the three ducts 12 associated with each pair of endpieces. Each duct 12 is in fluid communication with its associated bellows and together therewith it constitutes an assembly that is leakproof relative to the other ducts and bellows.

All of these elements of the device are enclosed in a flexible sheath 14 that can be connected in leakproof manner to the distal endpiece 6a. The spacing between the two endpieces 6b and 6c is maintained whatever the configuration of the device by means of spacers 16 contiguous with the sheath 14 and bearing against the facing axial ends of the endpieces 6b and 6c. The length of the spacers can be selected so as to obtain a predetermined spacing between the endpieces 6b and 6c. Alternatively, one of these two endpieces 6b and 6c could be omitted so as to cause the distal endpiece of one of the modules to form the proximal endpiece of the other module.

The sheath 14 can slide so as to leave space between the endpieces 6b and 6c, thereby enabling the endoprosthesis that is folded up in said space to be released. As a result, the sheath 14 need not be connected to the distal endpiece 6a in leakproof manner. The three feed ducts situated between the endpieces 6b and 6c can be closer together radially than the other three ducts so as to leave a large amount of peripheral space between the endpieces 6b and 6c.

The bellows are elastic and can be lengthened, shortened, and/or curved. The device has means 18 for injecting a fluid under pressure, in this case a liquid such as physiological serum, into each of the ducts 12 (and the associated bellows). These means make it possible to determine the pressure in each of the bellows independently of the other bellows. Such pressure feed and control means are known per se and are not shown in detail. In rudimentary form they could be constituted by a set of six declutchable non-return syringes associated with respective ones of the various ducts 12. In a more elaborate form, these means could be constituted by a distributor valve suitable for feeding the various ducts as a function of a general curvature command given by a suitable device, e.g. a keypad, a joystick, or even voice command. These control means are located at a distance from the endpieces and remain outside the body in the present case of medico-surgical exploration.

In this case, they are provided so as to be able to lengthen and shorten along their longitudinal direction under the effect of the fluid without substantial modification of a radial dimension of the bellows.

There follows a description of how the module 4 is deformed. To lengthen it without curving it, it suffices to increase the pressure in each of the bellows 10 so that the instantaneous pressure is the same in all three bellows. Similarly, decreasing the pressure uniformly in all three bellows will shorten the module. To curve the module, it suffices to deliver higher pressure to one or both bellows $10_1$ situated on the side opposite from the center of curvature O as shown in FIG. 5. Thus, these bellows lengthen so as to become longer than the other bellows $10_2$, thereby causing relative inclination to be established between the endpieces 6 and causing the device to curve. Naturally, both of those deformations can be combined within the same module so as to cause its length and its curvature to vary simultaneously.

The six control ducts 12 enable each stage to be deformed in completely independent manner as shown in FIG. 6 where the two stages are curved in a common plane but in opposite directions. Specifically, each stage can be controlled independently of the other. Furthermore, each of the six bellows can be controlled independently of the others. When both stages are shortened or lengthened simultaneously, these deformations are cumulative. The device of the invention possesses active compliance since it is possible to control and monitor its deformation via a control system. It also possesses passive compliance since it can be deformed to some extent under the effect of external forces. Thus, the higher the pressure in the ducts, the stiffer the device. Conversely, the lower the pressure, the more the device will become flexible and compliant. The device thus presents combined compliance, i.e. both passive and active. The working pressures can be selected to be higher or lower than the pressure of the ambient medium.

The deformations obtained by such a device are greater than those which can be obtained with a device that is controlled by cables only, in particular because cables generally work in traction. In contrast, the present device can be controlled in such a manner that at least one of its bellows is working under raised pressure while the other is working under lowered pressure such that their combined actions both serve to curve the stage in the same direction.

The device presents an empty central space on its axis 8, which space is uninterrupted along the entire length of the device. This space extends between the bellows 10, between the ducts 12, and it is defined by respective central orifices through the endpieces 6. This space can be used to house any selected instrument, tool, camera, liquid injection hose, electric cables, optical fibers, light rays, laser beams, viewing device, surgical instruments, needles, biopsy needles, fastening devices, etc. (clamps, clips, chisel, . . . ).

Each module 4 can be miniaturized so as to be of a length shorter than 2 cm and of a diameter less than 5 mm.

The embodiment of FIG. 4 is close to the preceding embodiment. Nevertheless, it differs therefrom in particular by the fact that each bellows 10 and its associated duct 12 has a cable 20 passing, in this case coaxially, therealong. The cable is fixed to the endpiece 6a or 6c to which the closed distal end of the bellows is also fixed. The control means 18 make it possible to pull at will on any one of the cables 20 without acting on the other cables. The device can be deformed by acting on pressure alone as before, by acting on the cables alone, or by acting on both simultaneously, thereby making it possible to obtain deformation in terms of length and curvature that is particularly marked and of variable stiffness.

Thus, the module can be shortened by reducing the pressure in the bellows. It can also be shortened by exerting an equal traction force on three control cables. In order to curve the module, the pressure can be varied from one bellows of the module to the other, as explained with reference to the first embodiment. In addition, the bellows $10_2$ can simultaneously be shortened by traction on the cables, thereby increasing the overall curvature of the device. The combination of the effect of the pressure and of the cable traction in each bellows enables the stiffness of the device to be varied.

In each of these embodiments, it is possible to avoid the risk of the bellows 10 buckling by surrounding each of them with a cylindrical spacer 22 that is shorter than the shortest design length of the bellows, as shown in chain-dotted lines in FIG. 2.

In the embodiment of FIG. 4, the device has two sheaths (this feature is independent of the presence of any cables). It has a second sheath 24 coaxial with the first sheath 14 and contiguous with the inside thereof, the sheath 24 being fixed to the proximal end face of the proximal endpiece 6d and extending towards the control means 18. These two sheaths can slide one in the other as a function of the movements of the distal endpiece 6a relative to the proximal endpiece 6d. This makes it possible to retract the outer sheath while holding the inner sheath longitudinally in position.

The (outer) sheath 14 can slide over the (inner) sheath 24. The sheath 24 serves to hold the device as a whole in longitudinal position since when it is prevented from moving, the endpiece 6d bears against it and therefore cannot reverse while the sheath 14 is shrinking.

A third embodiment is shown in FIGS. 7 and 8. In this case also, the device includes two stages 4, each stage having two main endpieces 6. Each stage further includes an additional and intermediate endpiece 7 midway between the two endpieces 6 and lying on the same axis. In each stage, each of the three bellows is replaced by a pair of bellows 10 extending in line with each other, in fluid communication with each other, and on either side of the intermediate endpiece 7. Each of the bellows 10 is therefore connected firstly to one of the main endpieces 6 and secondly to the intermediate endpiece 7.

Replacing each bellows of the first embodiment by two bellows disposed in series and controlled simultaneously allows the variation in length and in curvature of each stage to be increased in amplitude.

Furthermore, the intermediate endpiece 7 provides a spacer function, thereby preventing the bellows from buckling, which could occur if the bellows of the first or second embodiment were very long.

Furthermore, in this embodiment, each stage is associated exclusively as a group with six cables 20. The entire device therefore includes twelve cables 20. In this case, the cables extend out of the bellows and the ducts 12. Each pair of bellows is associated with two cables extending on either side of the bellows as can be seen in FIGS. 7 and 8. FIG. 7 shows one of the main endpieces 6 of the proximal stage 4, i.e. the stage shown at the bottom left in FIG. 8. The endpiece presents six main orifices 30 that are uniformly distributed around the central axis 8 of the endpiece and of the central channel 32. The orifices 30 at opposite ends of the endpiece correspond to the bellows 10 of the proximal stage or to the ducts 12 of the distal stage.

The endpiece presents twelve secondary orifices 34 associated in pairs with the main orifices and extending in the vicinity of said main orifices. The secondary orifices serve to receive the cables of the two stages. Naturally, on the endpieces of the distal stage, the number of main and secondary orifices can be reduced by half so as to avoid having unused orifices.

In this embodiment, each cable 20 is movable relative to all of the endpieces 6, 7. For each main endpiece to which each cable 12 is designed to be effectively connected, the cable carries a block 36 formed, for example, by a knot in the cable or by a part bonded or welded to the cable. The block prevents the cable from sliding in a certain direction and beyond a certain limit in the orifice 34 of the associated endpiece. Each cable carries two blocks disposed so that the cable limits the distance through which the two associated endpieces can move apart.

Each of the most distal blocks is used when it is desirable to shorten the device. The two blocks of each cable serve, in co-operation, to prevent plastic deformation of the bellows during a lengthening maneuver.

FIG. 9 shows a fourth embodiment which constitutes a variant of the third embodiment. This time, each endpiece carries six secondary orifices 34 instead of twelve. The six orifices are disposed in three pairs around three main orifices 30 associated with the proximal stage. They also serve to receive six associated cables. The six cables associated with the distal stage pass, this time, into the central channel 32 at the proximal stage. They occupy the six secondary orifices at the distal stage.

The endpieces can be made of a metal, a plastics material, or a composite material. The bellows can be made of a metal, a plastics material, or a composite material. The bellows can be secured to the endpieces in leakproof manner by adhesive, brazing, soldering, screw fastening, riveting, . . . The same applies to the hoses for feeding fluid under pressure which must be flexible and capable of withstanding the maximum pressures that the bellows can accept.

The endpieces can also possess recesses for purging air from the volumes under pressure (bellows 10, feed hoses 12) when using fluids other than air, and in particular when using liquids. These recesses can be closed by plugs so as to seal them after purging. The endpieces can also present recesses for receiving sensors or systems for receiving tools, of the forceps, cutting forceps, scissors, clamp, needle carrier, biopsy needle, suction nozzle, etc. type.

The device may have position sensors, e.g. ultrasound sensors for making it easier for the operator to guide it from the outside.

The cables can be made of shape memory alloy so as to lengthen or shorten under the action of temperature variations.

The bellows preferably have electroplated nickel.

The positioning device of the invention can be designed for single use (to be discardable).

Because the endpieces can move in translation and in rotation relative to one another, numerous applications can be envisaged.

1) In the Medico-Surgical Field
    making endoscopes of curvature that can be modified so as to follow the meanders of the natural passages to be explored, with steerable ends suitable for carrying a microcamera, an optical device, for directing a laser beam or any other type of wave or tool in a given direction (within the limits of the movements that are possible) (biopsy needles, injection needles, scissors, forceps, clamps, suction nozzles, electric scalpel, etc.);
    making catheters possessing the same properties as the above-described endoscopes; and
    making laparoscopy or celioscopy instruments fitted with surgical instruments.

2) In the Industrial Field
    In this field, since the size of the device is not a limiting factor, it can lie in the range a few millimeters to several decimeters. Applications are as follows:
    making devices for exploration and intervention in pipework;
    making grasping fingers for robot hands or manipulators for the handicapped;
    making legs for walking robots or for walking vehicles. The ability of the modules to lengthen and shorten, combined with transverse movements in two perpendicular directions make it possible, for example, for a four-legged vehicle to move both longitudinally and sideways;
    making devices for steering mirrors, waveguides, optical fibers, light or laser beams, etc. in three dimensions;
    making joints of variable stiffness interconnecting two solid members; and
    making a rotary coupling of controllable inclination. For example, a drilling device could be devised comprising a system for rotating and advancing a drilling tool (when drilling for oil or in other circumstances). If the drilling tool (bit, cutter) is coupled to the device for imparting rotation via a coupling whose deformation is programmed and synchronized with the rotary movement of the tool, it is possible to drill along a curved line, and this is sometimes desired in order to make it possible to drill horizontally starting from a conventional platform for drilling vertically.

Other applications can be envisaged in numerous other fields, whenever it is desirable to be able to steer one solid in three dimensions relative to another.

Naturally, numerous modifications can be applied to the invention without going beyond the ambit thereof. The number of stages can be one, two, three, or more. The number of bellows per stage can be equal to two, three, or more.

In the embodiments described above, although less advantageous, it is possible to provide for the bellows in the two stages to be connected together in series, at least in pairs, so that there are only three ducts 12, each controlling two bellows, i.e. at least one bellows in each stage. Naturally, under such circumstances, those two bellows can no longer be controlled independently of each other. However, the amplitude of axial deformation of each bellows and the lengthening of each module is increased.

The wall of each bellows could have a profile having a shape that is different from the ziz-zag shape shown in the figures. The wall could be a cylindrically shaped wall provided to present elasticity in the longitudinal direction but not in the radial direction.

The cables could be made of any plastics material, in particular polymer such as nylon, dacron, kevlar, or could be made of metal.

Figure 11:
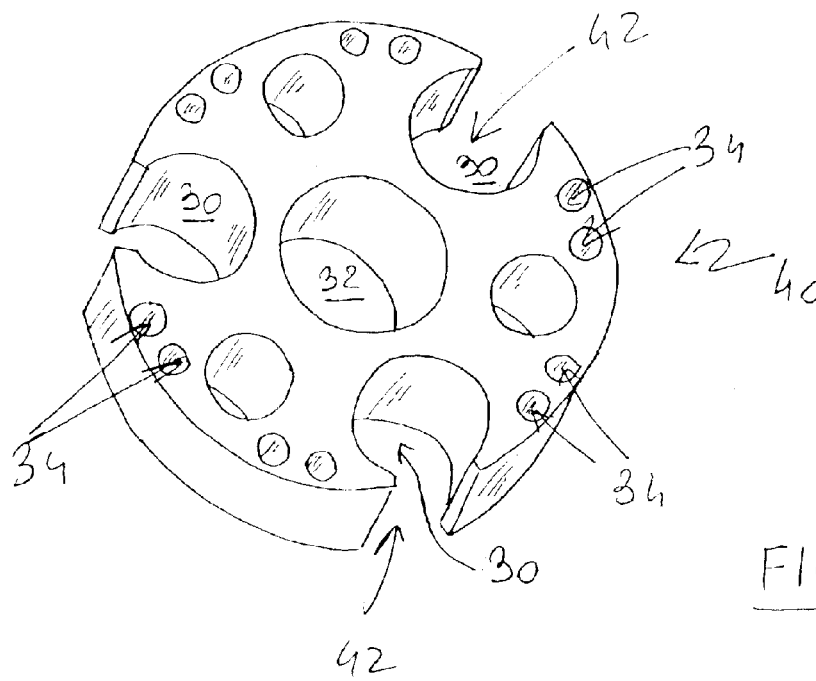
FIGS. 11 and 12 are perspective views respectively of a spacer and a bellow of the fifth embodiment.
Figure 12:
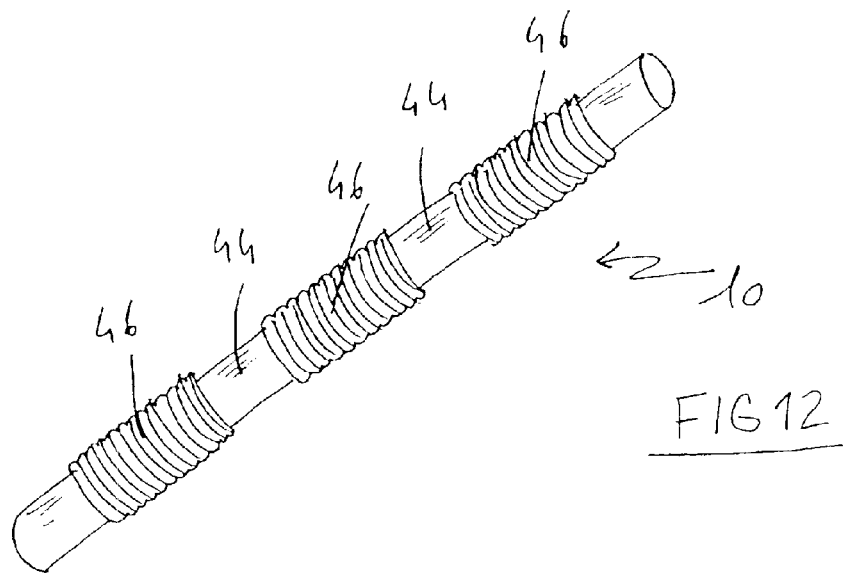

A fifth and preferred embodiment of the invention is shown on FIGS. 10 to 12.

This embodiment is very close to the previous ones and the same elements have the same numeral references.

Here, between any couple of endpieces following each other, for example the endpieces 6b–6c, the device comprises at least one and preferably at least two radial spacers 40. The two spacers are aligned with the two endpieces along axis 8 so that the order of the succession is: endpiece 6b, spacer 40, spacer 40, endpiece 6c. One of the spacer is disposed at one third of the length between the endpieces, and the other spacer at two thirds of this length. Each spacer 40 roughly has the same shape as the endpieces 6b, 6c but is shorter along axis 8. Its shape in plan view is a disc. It has the central channel 32 and three orifices 30 for housing three bellows respectively, bellows which extend from endpiece 6b to endpiece 6c, these orifices 30 being smaller in diameter than the channel 32. It also has ten orifices 34 for the respective cables 12. The three orifices 30 are open laterally on their side directed toward the radial periphery of the spacer. But the corresponding opening 42 is small enough to forbid the bellow from exiting the orifice laterally.

Each bellow 10 passes through both spacers 40. It shows two portions 44 aimed to extend inside the orifices 30, adjacent the respective spacers. Each portion 44 is smooth and deprived of corrugation, contrary to the other portions 46 of the bellow extending between the spacers or between a spacer and an endpiece. The diameter of the smooth portions 44 is smaller than the diameter of the portions 46.

These spacers are aimed to prevent any of the bellows from moving radially with reference to the longitudinal axis 8, that is to say from moving in any direction perpendicular to axis 8. Their presence permits to reduce the total width of the device.

An advantage of the device according to the invention is generally that it uses no electrical current for moving the device. Accordingly, it can be introduced in a duct of a human body without any danger. Beside, no electrical interaction risks to alter the working of another medical device, such as an imaging scanner used to follow the path of the device inside the body.

Advantageously, the device will include at least one force sensor and/or at least one sensor for measuring distance in order to detect a contact of the device with a wall of the duct and make easier to precisely locate at least one part of the device.

What is claimed is:

1. A positioning, intervention, and/or exploration device having two endpieces (6a–6d, 7) and at least one cable (20) extending from one endpiece to the other (6a–6d, 7), said at least one cable (20) being movable relative to at least one of the endpieces (6b, 6d), the device being characterized in that it comprises at least two bellows (10) each fixed directly to the two endpieces, and means (12, 18) for modifying the pressure of a fluid in each of the bellows independently of the other bellows.

2. A device according to claim 1, characterized in that it comprises at least three bellows (10) each fixed to the two endpieces (6a–6d, 7).

3. A device according to claim 1, characterized in that said at least one cable (20) is fixed to one of the endpieces (6a–d, 7).

4. A device according to claim 1, characterized in that said at least one cable (20) is off-center relative to the longitudinal axis (8) of the device.

5. A device according to claim 1, characterized in that said at least one cable extends outside the bellows (10).

6. A device according to claim 1, characterized in that it includes feed tubes (12) for feeding the bellows (10) with fluid, said at least one cable (20) passing outside the tubes (12).

7. A device according to claim 1, characterized in that said at least one cable (20) carries at least one block (36) suitable for coming into abutment against at least one of the endpieces during certain deformations of the device.

8. A device according to claim 1, characterized in that said at least one cable (20) carries at least two blocks (36) suitable for coming into abutment in two opposite directions against the two endpieces (6a–6d).

9. A device according to claim 1, characterized in that the cables (20) are two in number per bellows and are disposed on either side of the bellows.

10. A device according to claim 1, characterized in that it has at least three endpieces (6a–6d) disposed in succession, and for each successive pair of endpieces, it has at least two bellows (10) each fixed to two endpieces.

11. A device according to claim 10, characterized in that for each successive pair of endpieces it includes means (12, 18) for modifying the pressure of a fluid in each of the bellows (10) fixed to the endpieces of the pair, and for doing so independently of the other bellows fixed to the endpieces of the pair.

12. A device according to claim 10, characterized in that the means for modifying the pressure are suitable for modifying the pressure in each of the bellows fixed to the endpieces of one of the pairs, and for doing so independently of the bellows fixed to the endpieces of the other pair or of another pair amongst the pairs of endpieces.

13. A device according to claim 10, characterized in that the two bellows of one of the pairs of endpieces are in fluid communication with the respective bellows of the other pair or of another pair amongst the pairs of endpieces.

14. A device according to claim 1, characterized in that it includes at least one spacer (16) disposed to prevent two endpieces moving closer together or to prevent two of the endpieces moving closer together beyond a predetermined value.

15. A device according to claim 1, characterized in that each bellows is capable of lengthening and of shortening along a longitudinal direction of the bellows under the effect of the fluid without substantial modification of the dimension of the bellows perpendicularly to the longitudinal direction.

16. A device according to claim 1, characterized in that it has an inner first sheath (24) fixed to a proximal one (6d) of the endpieces, and an outer second sheath (14) receiving the endpieces (6a–6d) and suitable for sliding in the inner first sheath.

17. A device according to claim 1, characterized in that the fluid is a liquid.

18. A device according to claim 1, characterized in that it has an empty longitudinal space extending from one end of the device to the other.

19. A device according to claim 18, characterized in that the empty longitudinal space is arranged to allow instruments or waveguides to be passed therealong.

20. A device according to claim 1, the endpieces defining a longitudinal direction, the device including at least one spacer disposed between the endpieces and arranged to prevent at least one of the bellows against radial movement with reference to the longitudinal direction.

21. A device according to claim 20, wherein each spacer is arranged to prevent at least two bellows against the radial movement.

22. A device according to claim 20, wherein it includes at least two spacers arranged to prevent at least one of the bellows against the radial movement and both disposed between the two endpieces or between two of the endpieces following each other.

23. A device according to claim 20, wherein bellow prevented against radial movement by the spacer has a narrow portion adjacent to the spacer.

24. A device according to claim 20, wherein the or each bellow prevented against radial movement by the spacer has a smooth portion adjacent to the spacer.

25. A device according to claim 1, wherein said positioning, exploration, and/or intervention device is part of a medical-surgical instrument.

26. A device according to claim 1, wherein said device is part of a catheter.

27. A device according to claim 1, wherein said device is part of an endoscope.

* * * * *